(12) United States Patent
Reszka et al.

(10) Patent No.: US 7,556,827 B1
(45) Date of Patent: Jul. 7, 2009

(54) IMPLANTABLE ACTIVE INGREDIENT DEPOT

(75) Inventors: Regina Reszka, Schwanebeck (DE); Roland Schluter, Soest (DE)

(73) Assignee: Max-Delbrück-Centrum-für Molekulare Medizin, Berlin (DE)

( * ) Notice: Subject to any disclaimer, the term of this patent is extended or adjusted under 35 U.S.C. 154(b) by 52 days.

(21) Appl. No.: 10/048,840

(22) PCT Filed: Aug. 4, 2000

(86) PCT No.: PCT/DE00/02615

§ 371 (c)(1), (2), (4) Date: Apr. 8, 2002

(87) PCT Pub. No.: WO01/10411

PCT Pub. Date: Feb. 15, 2001

(30) Foreign Application Priority Data

Aug. 6, 1999 (DE) ................... 199 38 331

(51) Int. Cl.
*A61K 9/14* (2006.01)
*A61K 9/127* (2006.01)

(52) U.S. Cl. .............. 424/484; 424/450; 424/422

(58) Field of Classification Search .......... 424/450, 424/422–428, 484–489, 499–502
See application file for complete search history.

(56) References Cited

U.S. PATENT DOCUMENTS

| | | | |
|---|---|---|---|
| 5,008,109 A * | 4/1991 | Tin | 424/1.21 |
| 5,151,272 A * | 9/1992 | Engstrom et al. | 424/450 |
| 5,356,633 A * | 10/1994 | Woodle et al. | 424/450 |
| 5,531,925 A * | 7/1996 | Landh et al. | 252/299.01 |
| 5,665,700 A * | 9/1997 | Cho et al. | 514/2 |
| 5,891,456 A | 4/1999 | Shah et al. | |
| 6,638,621 B2 * | 10/2003 | Anderson | 428/402.24 |
| 6,699,499 B1 * | 3/2004 | Aneja | 424/450 |

FOREIGN PATENT DOCUMENTS

| | | |
|---|---|---|
| DE | 44 30 593 A | 2/1996 |
| DE | 197 24 796 A | 12/1998 |
| EP | 0 126 751 B1 | 5/1988 |
| WO | 93/19737 A | 10/1993 |
| WO | 96/39125 A | 12/1996 |
| WO | 98/47487 A | 10/1998 |

OTHER PUBLICATIONS

DeVita, V.T., "Principles in Chemotherapy", in Cancer : Principles & Practice of Oncology, Fourth Edition, Edition by DeVita, V.T. Samuel Hellman. Steven A. Rosenberg, J.B. Lippincott Co. Philadelphia 1993.*
Walter et al., Abstract of "Intratumoral Chemotherapy", Neurosurgery, vol. 37, No. 6, pp. 1129-1145, 1995.
S. Engstrom, "Drug Delivery from Cubic and Other Lipid-Water Phases", Lipid Technology, vol. 2, No. 2, Apr. 1990, pp. 42-45.

* cited by examiner

*Primary Examiner*—Gollamudi S Kishore
(74) *Attorney, Agent, or Firm*—Duane A. Stewart, III; Buchanan Ingersoll & Rooney PC

(57) ABSTRACT

The invention relates to an implantable active ingredient depot for therapeutically active substances. The fields of application are in medicine and the pharmaceutical industry. The implantable active ingredient depot is constituted of a lipid matrix capable of forming cubic phases into which modifier molecules have been integrated and contains pharmaceutically active substances. A preferred lipid matrix is monooleine. The implantable depot of the invention is useful for the treatment of tumors in oncological therapy and in gene therapy. A rational membrane design allows control of the release of the active ingredients over time and also control of the amount released.

2 Claims, 4 Drawing Sheets

RESULT OF THE CELL VITALITY TEST AFTER 72 HOURS OF TREATMENT OF F98 AND CC531 CELLS WITH THE MONOOLEINE CUBIC PHASE, 40% BY WEIGHT CP SOLUTION

RESULT OF THE CELL VITALITY TEST AFTER 72 HOURS OF TREATMENT OF F98 AND CC531 CELLS WITH THE MONOOLEINE/5 mol% MPEG-DSPE CUBIC PHASE, 40% BY WEIGHT CP SOLUTION

IMPLANTABLE ACTIVE INGREDIENT DEPOT

This application is the national phase under 35 U.S.C. § 371 of PCT International Application No. PCT/DE00/02615 which has an International filing date of Aug. 4, 2000, which designated the United States of America.

The invention relates to an implantable active ingredient depot for therapeutically active substances. The fields of application are in medicine and the pharmaceutical industry.

One aim of the pharmaceutical research entails making the supply of active ingredients to the patient as continuous as possible. For example, it is a great relief for diabetes sufferers to have depot insulin as a therapeutic at their disposal instead of the injections to be repeated many times a day. Recently, depot cytostatics (polymer-bound) have also been used as intratumoral release systems (Walter et al. Neurosurgery 37 (6) 1995 (Review) "Intratumorale Chemotherapie").

In EP 126 751 preparations containing a mixture of a biologically active material and one or more amphiphile substances are described, although these substances must be able to form a liquid crystalline phase together with other liquids. The most important amphiphile substance is monooleine, with the thermotropic and lyotropic mesophases with water in the foreground The objective of the preparations entails achieving slow and even release of the biologically active material (e.g. benzyl penicillin, insulin) at the place of effect and protecting it against disturbing interactions with the organism.

The preparations stated in EP 126 751 have been developed for a systemic application. This can also be seen from later publications by the authors, with the objective then being to reduce the size of the cubic phase to one suitable for systemic application (<10 µm) (S. Engström, Lipid Technology, Vol. 2, No. 2, April 1990, S. 42-45).

Further, the preparations have been developed only for an antibiotic application.

The aim of the invention is the application of gel-like cubic mesophases of the monooleine-water system as an implantable active ingredient depot for the treatment of tumours in oncological therapy and in gene therapy. A rational membrane design is to be developed in order to control the release of the active ingredients over time and to control the amount released.

This aim is achieved with the measures stated in the claims.

One essential benefit of the invention in question is that the active ingredient depot is completely biodegradable decomposable. It can be applied to open tissue (e.g. following operations) and adheres surprisingly well to mucous membranes. In this way, an active loco-regional treatment of tumours and the destruction of restenotic area are possible.

A further advantage is that the release of the pharmaceutically active substances can be controlled with regard to both the period and the amount depending on the modifier selected.

In the use of polyethylene glycol-modified lipids as a component of the active ingredient depot, a decisive extension of the release of the ingredient can be achieved in comparison with unmodified lipids. Fine control of the release can be achieved as a function of the length of the polyethylene chain. For example, a release of the active ingredient for 4 days is achieved with a length of the polyethylene chain of 500 units. If the polyethylene chain has a length of 2,000 units, the release of the active ingredient is extended to more than 7 days.

Brain tumours can hardly be treated with systemic chemotherapy as most substances are not capable of passing through the cerebral barriers. A local mono or poly-chemotherapy applied in the form of the gels (Carboplatin and Taxol) following surgical removal of the main tumour mass improves the prospects of a life-time extension with simultaneous maintenance of the quality of life.

Further, the active ingredient depot according to the invention can be used as a double release system for cytostatics for direct (local) chemotherapy.

The invention is to be explained below in more details on the basis of embodiments.

DETAILED DESCRIPTION OF THE INVENTION

"MPEG-DSPE" is an abbreviation for 1,2-distearoyl-glycerophosphatidyl-ethanolamin-methyl-polyethylene glycol.

Example 1.1

Measurement of the Release Rates

Determination of amount and velocity at which an enclosed active ingredient is released from a depot is decisive for the later in vitro and in vivo use of this system. Attempts must be made to develop an optimal form of release guaranteeing that the medication is available to insufficient amount to obtain a therapeutic concentration for a certain period—as a function of the particular medication. The system load must be kept as low as possible in order to avoid negative accompanying phenomena for the healthy tissue. For this reason, examinations have been made on the release kinetics of the slow-release system.

Figure 1:
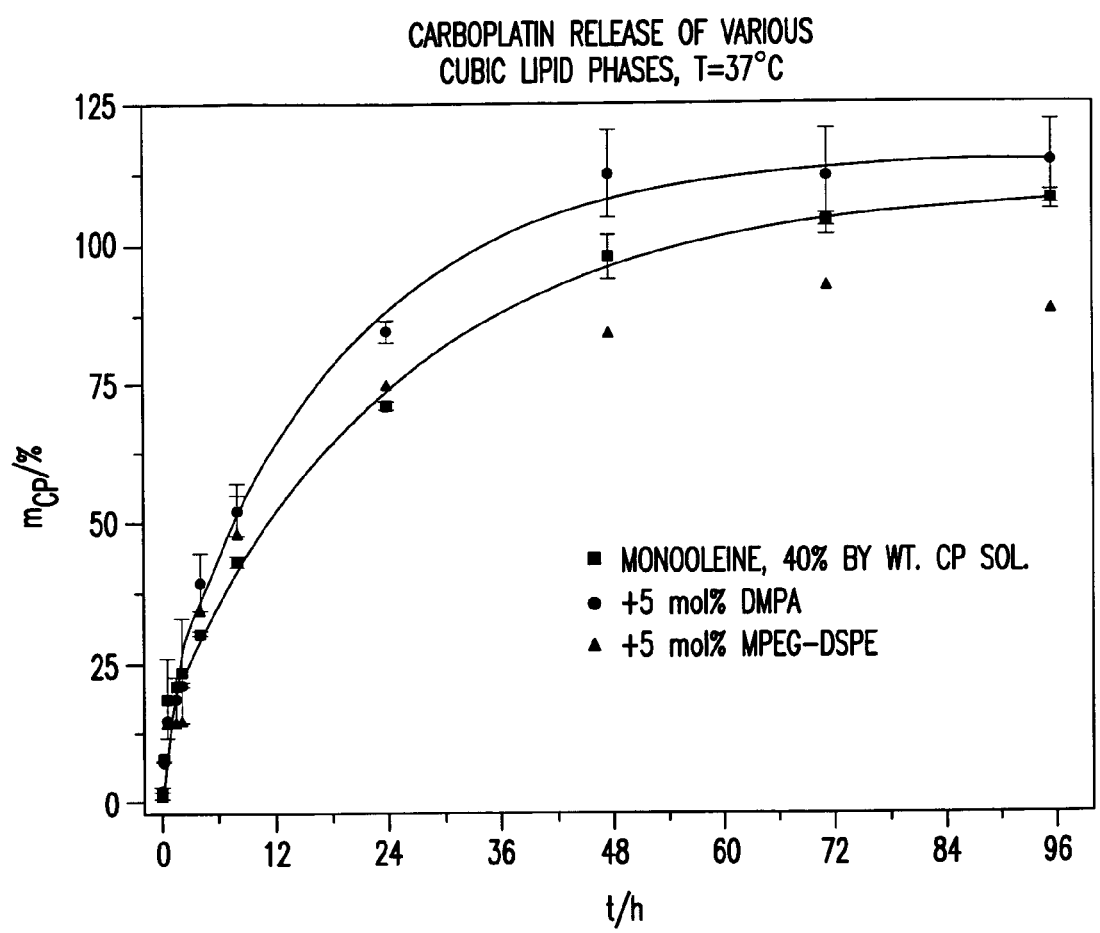
FIG. 1 shows a graph of carboplatin release of various cubic lipid phases.
Figure 2:
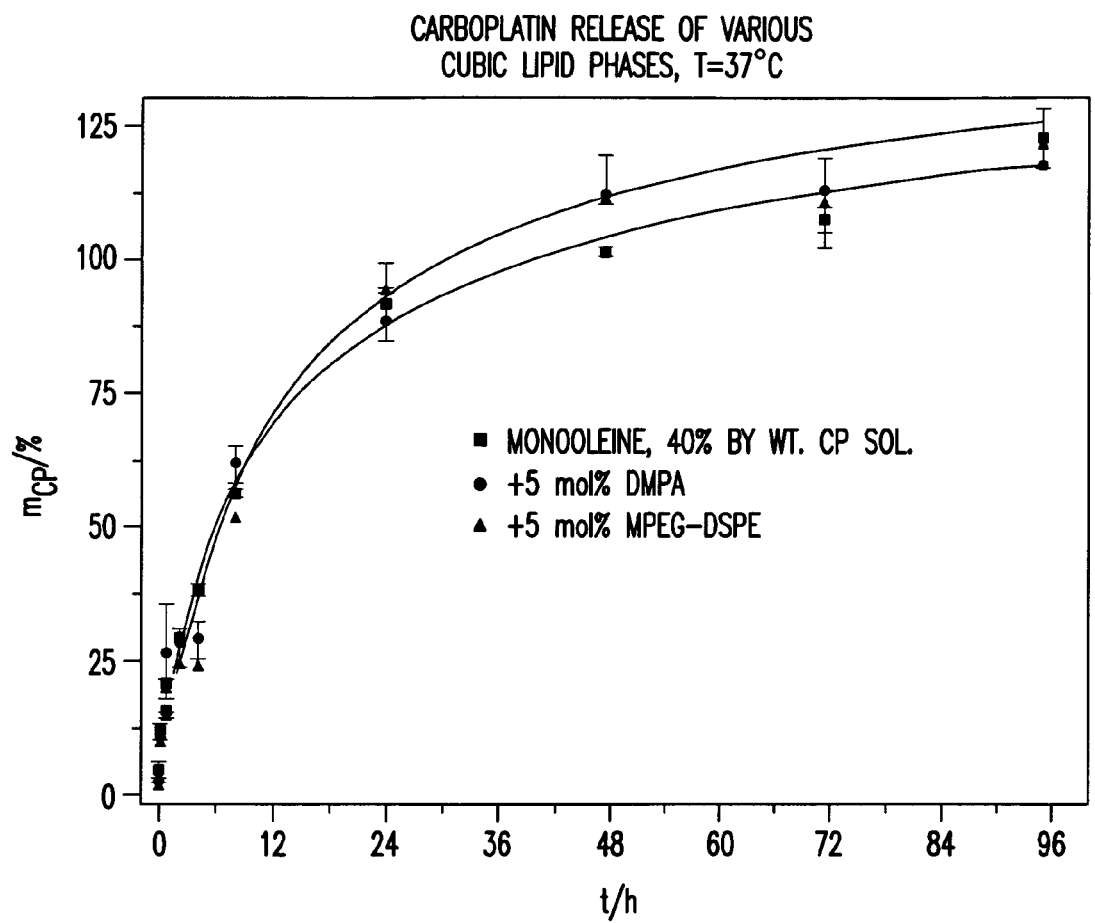
FIG. 2 shows a graph of carboplatin release of various cubic lipid phases at 37° C.

The measurement of the release kinetics was done on the cubic lipid systems and implantable active ingredient depots therefrom. The cubic phases exist in excess water and are thus relatively stable against contact with body fluids, e.g. blood or lymphatic fluid. In addition, the high viscosity makes them quite easily to handle and the systems manifest good adhesion to mucous membranes and other biological tissue, e.g. coating of nets. The system of three-dimensional water channels in the interior of the cubic phases leads to a water-soluble substance such as Carboplatin being incorporated in the water channels. It is thus protected against direct contact with body fluids and thus also against attacks by macrophages or enzymes and can thus diffuse relatively slowly out of the depot through the channels, where it is then available as an active substance. Important prerequisites are therefore that the water-soluble medication has the lowest possible interaction with the lipid membrane and that its structure—and thus its effectivity—is not altered by chemical reactions. Corresponding physical chemical measurements prove that these conditions are fulfilled by Carboplatin and the cubic lipid phases of monooleine or monooleine and MPEG-DSPE, as the case may be (FIGS. 1 and 2).

On the other hand, lipid-soluble active ingredients such as Taxol can be incorporated in the lipid phase. In this way, both a single and also a multi-component release system is possible (combination therapy).

If one assumes that the concentration of Carboplatin in the interior of the cubic phase is constant everywhere, the diffusion from the cubic phase is finally dependent upon the size of the border area between the sample and the surrounding medium and upon the volume of the phase per se, which with an—assumed—constant surface stipulates the amount of incorporated Carboplatin. Surface and volume of the sample are thus decisive geometrical factors influencing the release velocity. These parameters must therefore be selected as constantly as possible for a model system for the measurement of the release rate. For this reason, sample holders with a defined volume and a defined border area are used.

Example 1.1.1

Preparation of Samples 27 mM of Carboplatin (corresponding to 10 mg/ml bi-dist. water) are dissolved in bi-distilled water. After this, 5 g of monooleine are put into a vessel and melted in a water bath at about 45° C. 40% by weight of the CP solution is added to the melt and stirred with a spatula. This procedure is repeated 3 times, with the result that a homogeneous cubic phase is able to form. The closed containers are tempered at 40° C. for 24 h in order to achieve a quicker equilibrium.

The systems with a quantity of MPEG-DSPE or DMPA are prepared in an analogous way—however, 5 mol % of MPEG-DSPE or DMPA is added to the molten quantity of monooleine here. The powdery additional lipid is dissolved by severe shaking in liquid MO. After this, 40% by weight of CP solution is added again and the sample homogenised, as described above.

Example 1.1.2

Description of the Model System

236±3 mg of cubic phase is poured into a cylindrical sample vessel. This corresponds to a Carboplatin content of 8.2±0.1 mg per vessel. The filled sample vessels are suspended by their openings into a temperable volume of 4 ml of bi-distilled water, the contact area between the cubic phase and the surrounding medium being exactly 56.7 mm$^2$ for each sample vessel. Three measurements are made for each of them at 25 and 37° C. with the sample being shaken. At defined intervals, a small amount of the supernatant (50 µl) is removed and tested for its Carboplatin content by means of HPLC.

The so-called reverse-phase HPLC is used to determine the Carboplatin. Acetonitril with 0.015% phosphoric acid in a ratio of 89:11 (v/v) is used as the mobile phase. The separation is achieved via a MERCK LiChroCart 2504 column 25 cm in length (MERCK, Darmstadt) with a particle size of 5 µm and the Carboplatin determined by means of UV detection at 229 nm and a throughflow rate of the mobile phase of 1 ml/min (FIGS. 1 and 2).

Example 1.2

Measurement of the Anti-Neoplastic Effectivity In Vitro

In the following step, examinations showing the effect of such a depot form on living systems are made. F98 tumour cells sensitive against Carboplatin are used. Cell lines of a rat glioblastom, the so-called F98 cell line and of a rat colon carcinoma CC531 are used.

Example 1.2.1

Preparing the Samples

The preparation of the samples is identical with the mode of procedure described in Example 1.1.1. Samples containing various Carboplatin concentrations are used (0, 5, 10, 20 and 40 µg Carboplatin per 300 mg cubic phase). In comparison with the measurement of the release kinetics of the models, very low Carboplatin concentrations are used as the biological systems react extremely sensitively to the cytostatic.

1.2.2 Description of the Model System 1 ml (5×10$^6$ cells) of each of the individual cell suspensions are put into a 24-well micro-titre plate and special Transwell® chamber inserts (COSTAR, Netherlands) suspended into the individual chambers of the micro-titre plate. The inserts are implemented with 308±7 mg cubic phase (diffusion area of 33.2 mm$^2$) in each case. The incubation of the micro-titre plates is done for 72 h at 37° C. and 5% by vol. addition of $CO_2$ to the air. After the 72 h, the cell vitality is determined by means of an acid phosphatase assay.

Figure 3:
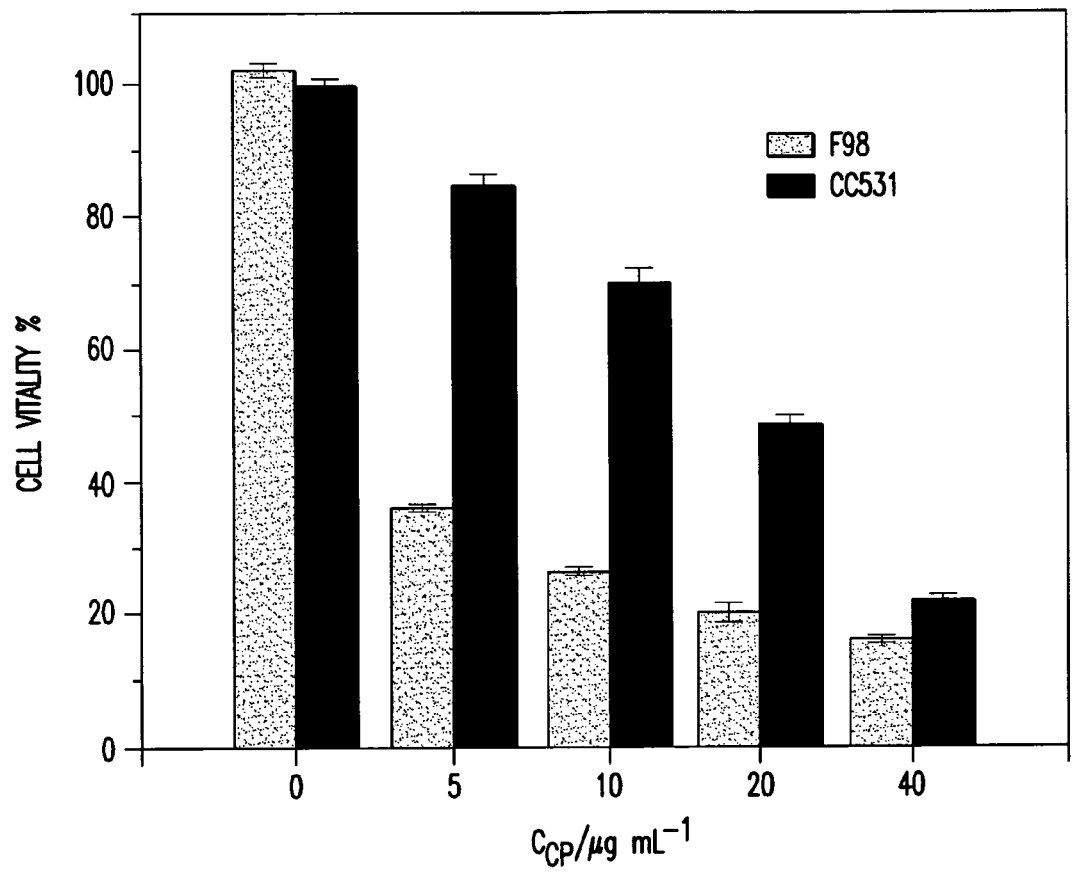
FIG. 3 shows the result of a cell vitality test after 72 hours of treatment of F98 and CC531 cells with the monooleine cubic phase.

FIG. 3 shows that the monooleine release system, 40% Carboplatin solution by weight, has a cytotoxicity on the varying tumour cell lines F98 and CC531. The colon carcinoma cells obviously react distinctly less sensitively to Carboplatin. Here, it was seen that a very much higher quantity of Carboplatin (5 µg of Carboplatin has killed off about 65% of the cells after 72 h) is necessary in order to achieve the same cytotoxic effect as with the glioblastoma cells. In order to eliminate about 65% of the cells, about 30 to 35 µg of CP is necessary.

Figure 4:
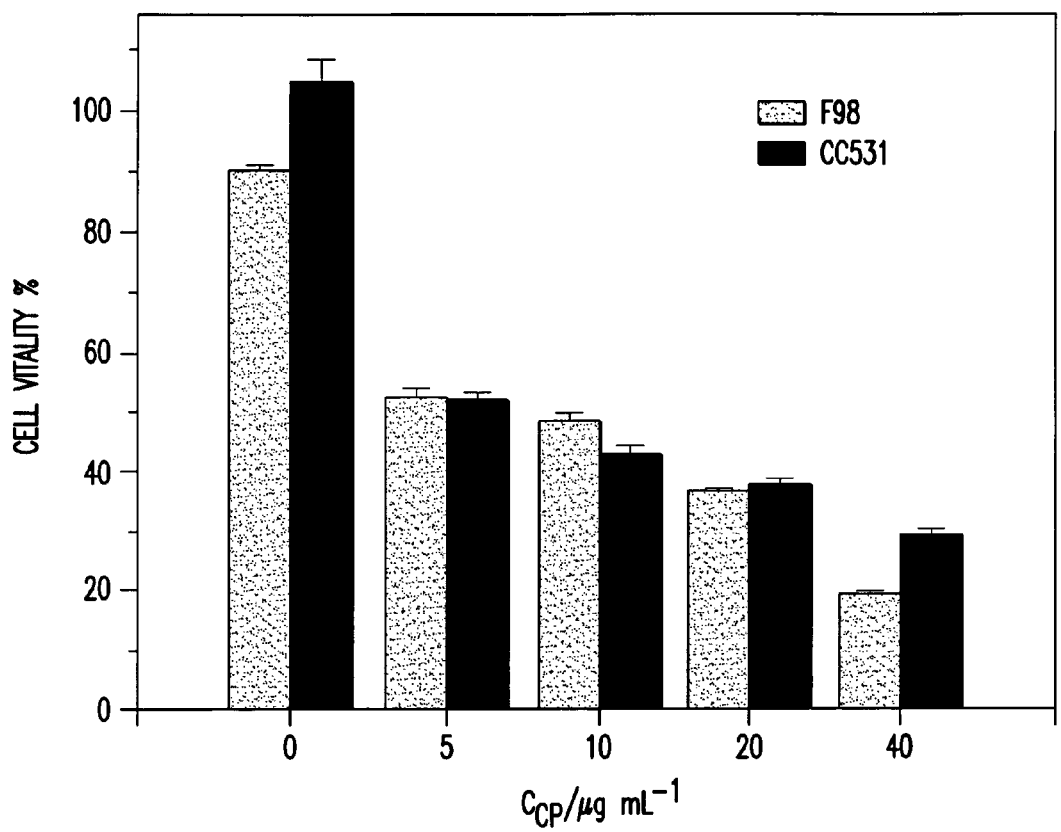
FIG. 4 shows the result of a cell vitality test after 72 hours of treatment of F98 and CC531 cells with the monooleine/5 mol % MPEG-DSPE cubic phase, 40% by weight CP solution.

In FIG. 4, the effect of the released Carboplatin on the tumour cell lines can clearly be recognised. In the F98 cell, the effect is comparable with the purely cubic system. A quantity of 5 µg of CP results in a cell elimination of about 65% after 72 hours. The colon carcinoma cells however react obviously more sensitively to the modified release system. Likewise, 5 µg of Carboplatin are sufficient to kill 65% of the cells.

If the two release systems are now compared with one another, one sees that the unloaded cubic phases manifest an insignificant to unmeasurable toxicity in each case. With a quite low amount of 5 µg of Carboplatin, much more than half the cells can be killed off in an in vitro experiment after 72 hours.

The invention claimed is:

1. An implantable active ingredient depot, wherein the matrix provides a controlled release of the active ingredient, comprising:
   i) a matrix comprising glyceryl-monooleate and at least one modifier molecule, wherein the modifier molecule is 1,2-distearoyl-glycerophosphatidyl-ethanolamin-methyl-polyethylene glycol (MPEG-DSPE), said matrix forming a cubic phase; and
   ii) a combination of Carboplatin as an active ingredient in the hydrophilic cubic phase and Taxol as an active ingredient in the hydrophobic lipid bilayer, wherein the release rates of the Carboplatin and Taxol are varied independently by varying the surface area and volume of the matrix and by varying the length of the polyethylene chain of the modifier molecule, respectively.

2. A method for delivering a combination of Carboplatin and Taxol as a therapeutic agent to a patient, comprising implanting an implantable active ingredient depot of claim 1 into a mucous membrane or into a surgically exposed tissue of the patient.

* * * * *